United States Patent [19]
Honda et al.

[11] Patent Number: 6,021,393
[45] Date of Patent: Feb. 1, 2000

[54] MEDICAL INFORMATION MANAGEMENT SYSTEM

[75] Inventors: Hiroto Honda, Tsurugashima; Shinichi Shiina, Tokyo, both of Japan

[73] Assignees: Nippon Conlux Co., Ltd.; Shinichi Shiina, both of Tokyo, Japan

[21] Appl. No.: 08/885,398

[22] Filed: Jun. 30, 1997

Related U.S. Application Data

[63] Continuation-in-part of application No. 08/543,466, Oct. 16, 1995, abandoned, which is a continuation of application No. 08/229,558, Apr. 19, 1994, abandoned.

[51] Int. Cl.[7] .............................................. C06F 159/00
[52] U.S. Cl. .............................................. 705/3; 235/487
[58] Field of Search ........................... 705/1–4; 235/379, 235/380, 440, 492, 488; 283/76, 112; 380/7, 46

[56] References Cited

U.S. PATENT DOCUMENTS

| | | | |
|---|---|---|---|
| 4,632,428 | 12/1986 | Brown | 283/76 |
| 4,665,004 | 5/1987 | Drexler | 430/140 |
| 4,870,682 | 9/1989 | Morrey et al. | 380/46 |
| 4,918,523 | 4/1990 | Simon et al. | 348/396 |
| 5,215,334 | 6/1993 | Presson | 283/76 |
| 5,291,399 | 3/1994 | Chaco | 235/375 |
| 5,530,232 | 6/1996 | Taylor | 235/380 |
| 5,578,415 | 11/1996 | Hayashi et al. | 430/270.11 |

FOREIGN PATENT DOCUMENTS

| | | |
|---|---|---|
| 3-154970 | 7/1991 | Japan . |
| 4-78959 | 3/1992 | Japan . |
| 4-98467 | 3/1992 | Japan . |
| 2 165 069 | 4/1986 | United Kingdom . |

OTHER PUBLICATIONS

Patent Abstracts of Japan, vol. 14, No. 17, C675, Abstract No. 01–259838, Shibuya et al; Abstract No. 02–120981, Kanazawa.

Optical Information Systems, Jul.–Aug. 1988, Brown et al., "A New Patient System Using the LaserCard" pp. 156–160.

*Primary Examiner*—Frantzy Poinvil
*Attorney, Agent, or Firm*—Graham & James LLP

[57] ABSTRACT

As a portable memory card carried by a patient to store the patient's personal medical information, a hybrid-type memory card is used which includes an optical information recording area, an integrated circuit memory area and a magnetic information recording area. A read/write drive for the memory card includes an optical head, a carrier mechanism for loading the memory card on a carrier table and moving the loaded memory card relative to the optical head, and a coupler section for coupling electronic information to be read and written from and to the integrated circuit memory area of the memory card, so that reading and writing of optical information from and to the optical information recording area can be conducted simultaneously with reading and writing of the electronic information from and to the integrated circuit memory area.

12 Claims, 5 Drawing Sheets

| A | CONTROL DATA |
| B | NAMES OF HOSPITAL & DOCTOR |
| C | PATIENT'S NAME & ADDRESS |
| D | CONTENTS OF CHART |
| E | VARIOUS TEST RESULTS |
| F | IMAGE INFORMATION |
| G | SOUND INFORMATION |

MEDICAL INFORMATION MANAGEMENT SYSTEM

RELATED APPLICATION

The present application is a continuation-in-part application of U.S. patent application Ser. No. 08/543,466 filed Oct. 16, 1995 under the title of "Medical Information Management System" now abandoned, which in turn is pending as a file-wrapper continuation of U.S. patent application Ser. No. 08/229,558 filed Apr. 19, 1994 now abandoned.

BACKGROUND OF THE INVENTION

The present invention generally relates to a medical information management system which records a patient's personal medical information onto an optical card for various management purposes.

Medical information management systems are popularly known, in which various character and image information such as characters, drawing, X-ray photograph and computer tomogram (so-called CT) originally entered in patients' case records (charts) as their personal medical information are optically or magnetically recorded onto recording media such as optical cards and magnetic disks. Such prior art medical information management systems are typically disclosed in Japanese Patent Laid-open Publications Nos. HEI 3-154970, 4-78959 and 4-98467.

Because the medical image information, in general, must be highly detailed and precise, recording, for example, a single X-ray photograph as a piece of image information usually requires a storage capacity of about one megabyte. In addition, in order for a doctor to obtain knowledge about or diagnose the morbid state of a given patient, image information corresponding to at least three X-ray photographs would be necessary. This means that a medium for recording the patient's medical information must have storage capacity of more than three megabytes.

Nevertheless, the storage capacity of today's commercially available optical cards is only about three megabytes at the most, and thus, even if some form of data compression technique etc. are employed, it is very difficult or impossible for the optical cards to record thereon more than two or three X-ray photographs of image information and character information (and/or drawing information) about the patient's personal identification, clinical history, doctor's observation and the like.

Further, in the case of a patient having a circulatory disease, the doctor may more easily obtain knowledge of or diagnose the morbid state of the patient by listening to the patient's characteristic cardiac sounds, cardiac murmurs etc., rather than by examining the patient's X-ray photograph. However, since the prior medical information management systems only express such patient's cardiac sounds, cardiac murmurs etc. in onomatopoeic words or in schematic diagram and then record these as character and image information, it is very difficult to promptly obtain knowledge about the patient's morbid state just by examining the thus-recorded character or image information.

SUMMARY OF THE INVENTION

It is therefore an object of the present invention to provide an improved medical information management system which is capable of efficiently recording medical information corresponding to a patient's morbid state onto an optical card having limited storage capacity.

In order to achieve the above-mentioned object, the present invention provides an improved medical information management system for recording a patient's personal medical information onto a recording medium to manage the medical information, the recording medium being a portable card-like medium independently provided for the patient. The medical information management system comprises: the recording medium including an optical information recording area and an integrated circuit memory area for storing electronic information; a read/write drive for removably attaching thereto the recording medium to read and write information from and to at least the optical information recording area and the integrated circuit memory area, the read/write drive including an optical head for reading and writing optical information from and to the optical information recording area, a carrier mechanism for loading the recording medium on a carrier table and moving the loaded recording medium relative to the optical head, and a coupler section for coupling electronic information to be read and written from and to the integrated circuit memory area of the recording medium, so that reading and writing of the optical information from and to the optical information recording area can be conducted simultaneously with reading and writing of the electronic information from and to the integrated circuit memory area; a controller for controlling the read/write drive so as to execute control to write any of character information, image information and sound information, corresponding to a morbid state of the patient, into the optical information recording area as the medical information, control to read out the medical information written in the optical information recording area, control to write a predetermined part of the medical information into the integrated circuit memory area and control to read out the predetermined part of the medical information written in the integrated circuit memory area; a display device for visually displaying the character information and image information contained in the medical information read out by the controller; and a reproduction device for audibly reproducing the sound information contained in the medical information read out by the controller.

The recording medium is a so-called "hybrid-type" card-like memory medium (hereinafter called an "optical card" for simplicity), which includes an optical information recording area and an integrated circuit memory area and may further include a magnetic information recording area such as a magnetic stripe. As medical information of the patient, any of character information, image information and sound information, corresponding to a morbid state of the patient, is recorded into the optical information recording area of the optical card. Suitable medical information may be recorded into the integrated circuit memory area. Additional information useful for assuring more reliable maintenance of secrecy of patient's information (patient's secret maintaining information) may be stored in the integrated circuit memory area, making use of a security function characteristic of the IC. As an example, the patient's secret maintaining information stored in the integrated circuit memory area may be compared with information prestored in a predetermined patient table possessed by a host computer, so as to control the usability of the optical card. Thus, the hybrid-type optical card having the optical and IC storage functions according to the present invention can be used quite extensively as a medical information recording medium and can appropriately meet a variety of needs in various medical fields. Because magnetic cards are employed in relatively many of the existing medical management systems, the additional provision of the magnetic information recording area on the optical card permits use of such an existing medical management system when necessary.

The present invention is further characterized by a novel arrangement of the read/write drive. Namely, the read/write drive includes an optical head, a carrier mechanism for loading the memory card on a carrier table and moving the loaded memory card relative to the optical head, and a coupler section for coupling electronic information to be read and written from and to the integrated circuit memory area of the memory card, so that reading and writing of optical information from and to the optical information recording area can be conducted simultaneously with reading and writing of the electronic information from and to the integrated circuit memory area.

The optical card is a nonvolatile memory which is very handy for carrying, has sufficiently large storage capacity (about three megabytes) and is very easy to write data thereon. For these reasons, the optical card is known as one of the most suitable recording media for recording patient's personal medical information. Thus, by using such an optical card as a recording or memory medium, it is possible to efficiently record medical information as needed depending on a specific morbid state of the patient. Therefore, if only the patient carries the optical card bearing his or her medical information to a given doctor, the doctor, by only setting the optical card in the read section, can read the patient's medical information, can have the character and image information visually shown and also can have the sound information audibly reproduced or sounded. This allows the doctor to readily obtain knowledge about the patient's morbid state.

The doctor can easily acquire or diagnose the patient's morbid state by listening to the patient's characteristic cardiac sounds and murmurs, particularly to the cardiac murmurs if the patient has a circulatory disease. Similarly to the cardiac murmurs, the respiratory or breathing sounds are very characteristic of, i.e., very faithfully reflect a disease. Thus, it is desirable to record the respiratory sounds as sound information so that the doctor can easily obtain knowledge about the patient's morbid state by audibly reproducing the information with the present system.

In the most preferred embodiment of the present invention, the sound information may be graphed as a visual sound waveform diagram as well as being audibly reproduced through the reproduction section. This allows the doctor to more clearly acquire the patient's morbid state both aurally and visually.

In addition, even when the patient goes to a hospital for the first time, the patient can let a doctor of the hospital readily know about his or her morbid state by only presenting the medical information bearing optical card and having it set in the read section of the system. Further, since only desired medical information depending on his or her own morbid state may be recorded on the private optical card and since it sometimes may not be necessary to record image information of a large data amount on the card, it is very often sufficient for the patient to carry only one optical card. This is far more economical than when the patient carries several optical cards.

Moreover, even in medical educational organizations, the medical information management system of the present invention can be applied as an effective means for morbid state acquisition, by reproducing the sound information recorded on the optical card.

The preferred embodiment of the present invention will be described in detail below with reference to the accompanying drawings.

DETAILED DESCRIPTION OF THE PREFERRED EMBODIMENT

Figure 1:
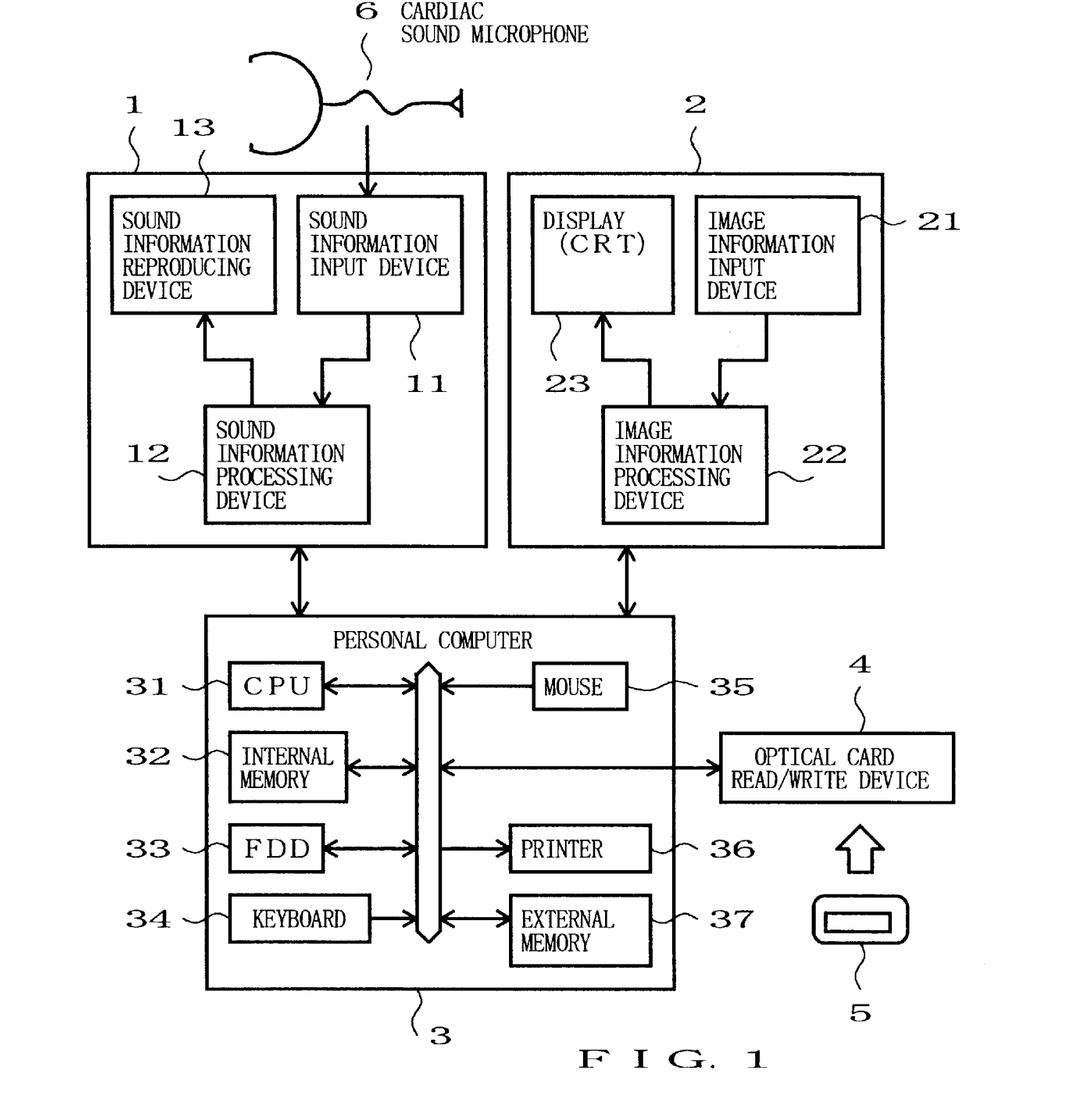
FIG. 1 is a block diagram illustrating the general structure of a medical information management system in accordance with an embodiment of the present invention.

FIG. 1 is a block diagram illustrating the general structure of a medical information management system in accordance with a preferred embodiment of the present invention. This management system generally comprises sound an information processing device 1, an image information processing device 2, a personal computer 3, an optical card read/write device 4 and an optical card 5 that is removably attached to or set in the optical card read/write device 4.

The sound information processing device 1 is composed of a sound information input device 11, a sound information processing board 12 and a sound information reproducing device 13.

The sound information input device 11, which includes a cardiac sound microphone 6, converts patient's cardiac sounds, cardiac murmurs or respiratory sounds into respective analog sound information signals, and then outputs the sound information to the sound processing board 12.

The sound information reproducing device 13, which may for example comprise a speaker, audibly reproduces the analog sound information signals received from the sound information processing board 12.

The image information processing device 2 is composed of an image information input device 21, an image information processing board 22 and a display device 23.

The image information input device 21, which includes a video camera or an FD camera (an electronic camera with a floppy disk drive), generates NTSC signals based on X-ray photograph information and outputs the NTSC signals to the image information processing board 22.

The image information processing board 22 converts the NTSC signals received from the image information input device 21 into digital image information and outputs the digital image information to the personal computer 3. The image information processing board 22 also converts digital image information received from the personal computer 3 into NTSC signals and outputs the NTSC signals to the display device 23. In addition, the image information processing board 22 receives digital sound information that is being provided from the personal computer 3 to the sound information processing board 12 of the sound information input device 11 and converts the input sound information into a sound waveform diagram in the form of NTSC signals. The sound waveform diagram is provided to the display device 23.

The display device 23 comprises a TV monitor such as a CRT display and visibly presents thereon the NTSC signals provided from the image information processing board 22. Namely, the image information processing board 22 outputs NTSC signals based on normal image information of X-ray photograph or the like and based on a sound waveform diagram that visually represents digital sound information, and the display device 23 presents thereon visual images corresponding to such information. For the sound waveform diagram, the display device 23 presents a corresponding graph.

The personal computer 3 controls the entire operation of the medical information management system, and it basically comprises a CPU 31, internal memories (ROM and RAM) 32, peripherals and I/O interfaces. As such peripherals, this personal computer 3 includes a floppy disk drive (FDD) 33, a keyboard 34, a mouse 35, a printer 36, an external memory (e.g. hard disk), etc. Further, the sound information processing board 12 and image information processing board 22 are attached, for example, to extension slots in the personal computer 3. Accordingly, the personal computer 3 also incorporates therein software programs that are necessary for executing various processes on the sound and image information by means of the sound information processing board 12 and image information processing board 22.

The optical card read/write device 4, which is connected to the personal computer 3 as one of the peripherals thereof, writes and reads data to and from the optical card 5 under the control of the personal computer 3.

The medical information management system which, as mentioned above, comprises the sound information processing device 1, image information processing device 2, personal computer 3 and optical card read/write device 4 is installed within a hospital. The optical card 5 is possessed by an individual patient and is set in the optical card read/write device 4 such as when the patient receives medical examination by a doctor.

Figure 2:
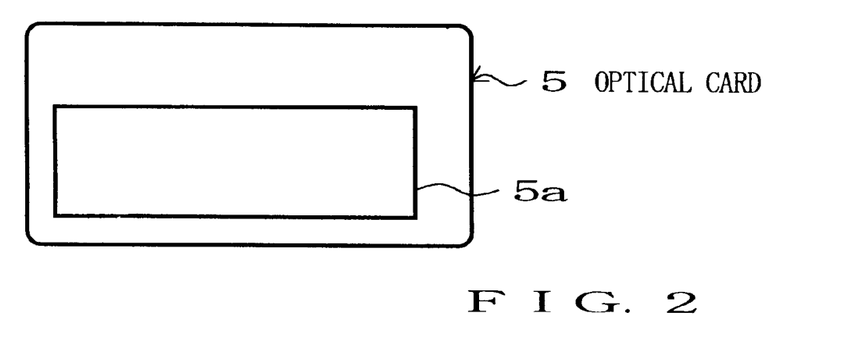
FIG. 2 is a top plan view illustrating an example of an optical card for use with the medical information management system of FIG. 1.

As typically shown in FIG. 2, the optical card 5 is a rectangular-shaped card having a size of about 85.6 mm length and about 54 mm width and has a thickness of about 0.76 mm. A predetermined area 5a on the card surface is a recording area, onto which digital data corresponding to the patient's medical information are optically recorded. The recorded digital data are then optically read out from the card when needed. Such an optical card 5 may, for example, be a DELA-standard card available from Drexler Inc. The optical card read/write device 4, which is designed to allow removable setting therein of the optical card 5, can optically write desired information (in this example, medical information comprising character, image, sound information etc.) onto the thus-set card 5 using light beams and read out the written information as needed.

In the case of the DELA-standard optical card, every new information is written as an addition into unrecorded portion of the recording area (in a write-once fashion). Specific examples of the optical card read/write device 4 and optical card 5 are disclosed, for example, in Japanese Patent Laid-open Publication Nos. SHO 58-500437, 59-195327, 61-48135, 61-137245, 62-256248, 62-262239 and 62-266748, and therefore a detailed description on these is omitted herein.

Figure 3:
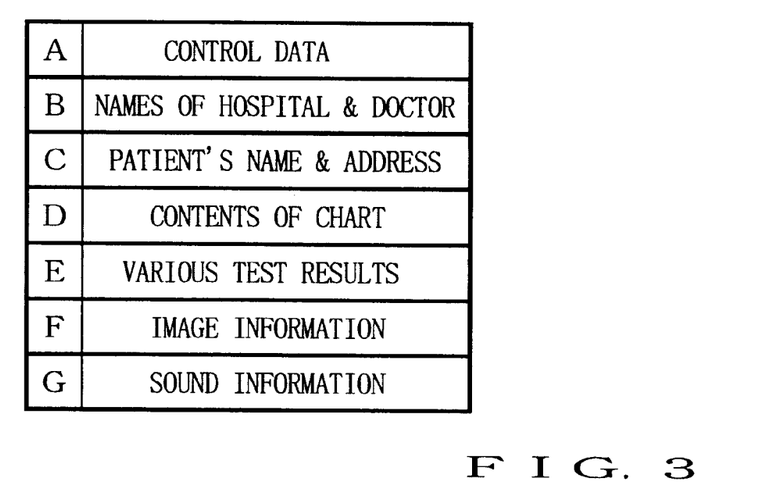
FIG. 3 is a diagram illustrating an example of recorded data on the optical card.

FIG. 3 illustrates an example of the medical information stored on the optical card 5. As illustrated, the recording area 5a of each optical card 5 is divided into a plurality of memory regions A–G for recording a plurality of data. On memory region A are stored control data that are indicative of the addresses and storage capacities of the individual memory regions. On memory region B, information such as the names of the hospital and doctor in charge of the patient is stored as character information. Further, on memory region C, personal information such as the patient's name and age is stored as character information. Further, on memory region D, contents of the patient's chart such as results of the doctor's questioning and diagnosis are stored as character information. Further, on memory region E, results of various tests such as urine analysis, blood type and blood pressure are stored as character information. Further, on memory region F is stored image information such as X-ray photograph and CT. Finally, on memory region G is stored sound information such as cardiac murmurs and respiratory sound detected by the above-mentioned cardiac sound microphone 6.

The hospital name, patient's disease name and blood type and results of various tests may be directly stored as character data. But, in order to save storage capacity, it is desirable that these data are stored in encoded form, in which case the encoded data are decoded by the personal computer 3 for subsequent necessary processing. The sound information may be PCM data obtained by subjecting analog sound waveform signals to a digital PCM conversion; however, this approach will require large storage capacity, and accordingly only a limited amount of the sound information can be recorded on a single optical card 5. It should be appreciated that, in order to save the storage capacity, the sound information may of course be stored in some data-compressed form by the use of DPCM, ADPCM or any other suitable sound data compression technique.

Figure 4:
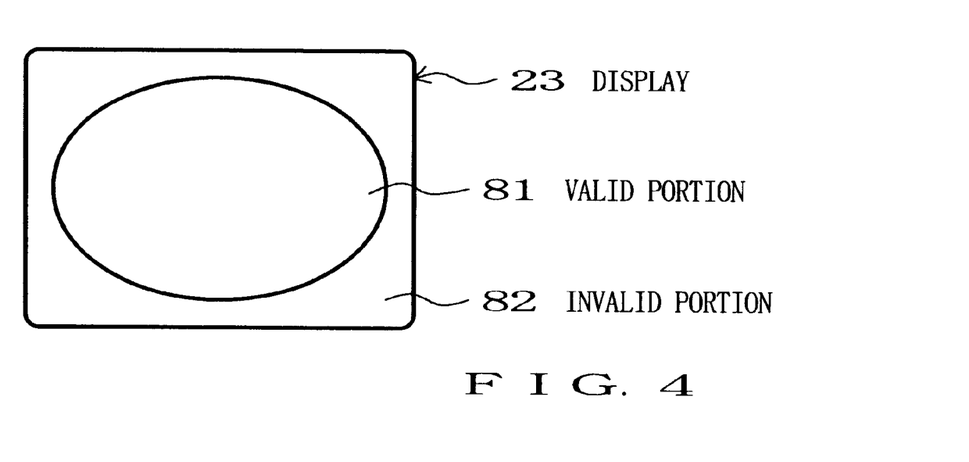
FIG. 4 is a diagram explanatory of a display state on a display device of FIG. 1.

Because of this, the embodiment attempts to minimize the required storage capacity by inserting the sound and/or character information in an invalid portion of the image information. For instance, as shown in FIG. 4, if image information generally of an elliptical shape is presented on the display device 23, the doctor only needs the valid portion 81 in order to acquire the patient's morbid state and does not need an invalid portion 82 surrounding the valid portion 81. Therefore, the sound and/or character information can be inserted in the invalid portion 82 without disturbing the valid portion 81, and thus, the storage capacity for the image information can be utilized efficiently. More specifically, in such a case where one frame of image information data is stored in a predetermined storage area of the optical card 5, it is possible that, instead of the image information being stored in the entire frame storage area, image information representing the valid portion 81 is stored in a part of the area corresponding to the valid portion 81, and sound information and/or character information is stored in the other part of the area corresponding to the invalid portion 82.

Figure 5:
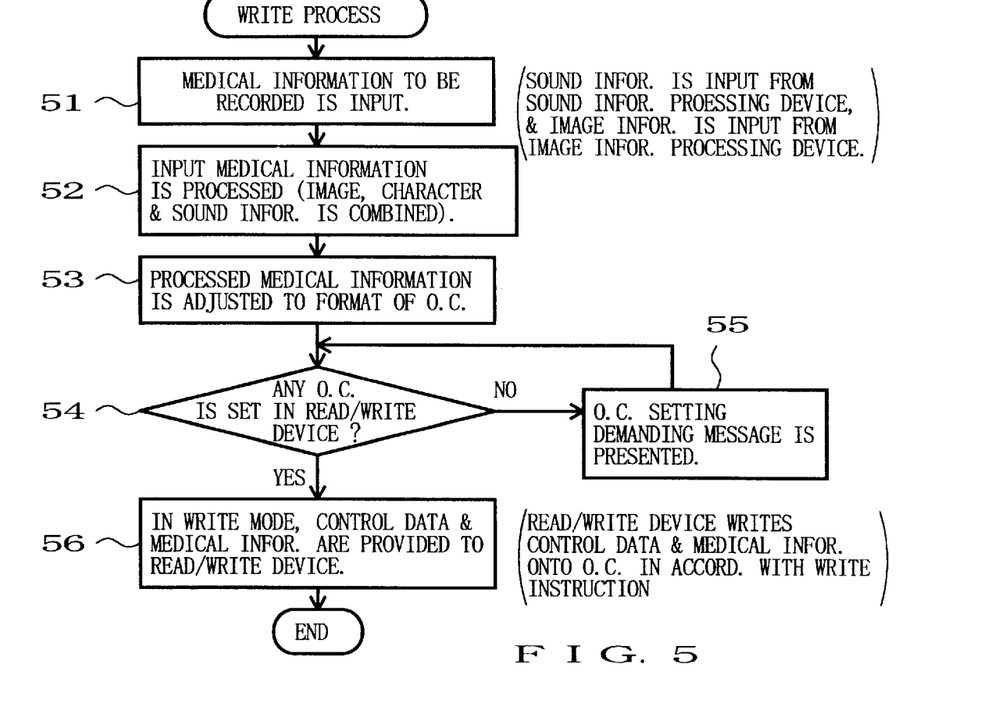
FIG. 5 is a flowchart illustrating an example of a write process carried out by the medical information management system of FIG. 1.

Now, an example of a write process carried out by the personal computer 3 for writing medical information onto the optical card 5 will be described with reference to a flowchart of FIG. 5.

Step 51: Medical information (character, image and sound information) of a given patient to be recorded onto the optical card 5 is fetched: the character information is input into directly from the keyboard 34; the image information is input from the image information processing device 2 as digital image information; and the sound information is input from the sound information processing device 1 as digital sound information.

Step 52: Any data processes necessary are applied to the respective medical information input in the manner mentioned above. For example, sound components other than the patient's cardiac sounds, cardiac murmurs and respiratory sounds may be filtered out, the sound and character information may be inserted in the invalid portion 82 of the image information as shown in FIG. 4, and/or, the image, character and sound information may be stored in a combined or composite form.

Step 53: The medical information as processed in step 52 above is adjusted to the recording format of the optical card.

Step 54: It is determined whether or not any optical card 5 is attached to or set in the optical card read/write device 4. The personal computer 3 goes to step 55 if the optical card 5 is not set, but goes to step 56 if the optical card 5 is set.

Step 55: Because of the negative determination in step 54 above, a message that demands setting of the optical card 5 is presented on the display device 23 or given in voice or the like.

Step 56: After preparation of the medical information to be written and control data indicating how to write the medical information is completed, the personal computer 3 waits for a write instruction signal to be input by operation of the keyboard 34 etc. Then, when the write instruction signal is input, the personal computer accesses the optical card read/write device 4 so as to write, onto the optical card 5, the medical information and control data that have been input previously. That is, when the write instruction signal is input, the personal computer 3 changes the operation mode into the optical card write mode and provides the control data and medical information to the optical card read/write device 4. The optical card read/write device 4 in turn writes the medical information and control data onto the optical card 5 in accordance with the write instruction signal. Namely, this write process writes the medical information and control data as addition to an unrecorded portion of the card rather than as a rewrite to an already recorded portion of the card. However, the medical information and control data may of course be written as a rewrite to the already written portion if a rewritable recording or memory medium is employed.

Figure 6:
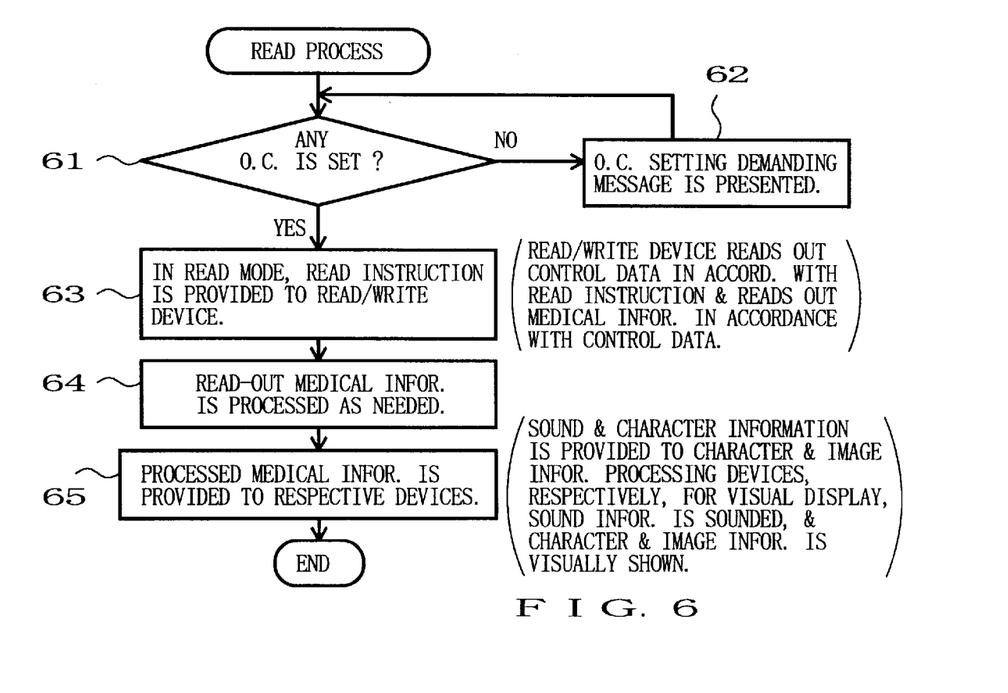
FIG. 6 is a flowchart illustrating an example of a read process carried out by the medical information management system of FIG. 1.

An example of a read process performed for the personal computer 3 to read out the medical information from the optical card will be described with reference to the flowchart shown in FIG. 6.

Step 61: A determination is made as to whether any optical card 5 is set in the optical card read/write device 4. The process goes to step 62 if the answer is in the negative, but it goes to step 63 if the answer is in the affirmative indicating that an optical card 5 is set in the read/write device 4.

Step 62: Because of the determination in the preceding step 61 that no optical card is set in the optical card read/write device 4, a message for demanding setting of an optical card is given on the display device 23 or in other suitable form such as vocal sound.

Step 63: When medical information to be read out is specified by the user's operation of the keyboard 34 or mouse 35, the personal computer 3 changes the operation mode into the optical card read mode and then provides the optical card read/write device 4 with a read instruction signal corresponding to the medical information to be read out. In response to the read instruction signal, the read/write device 4 reads out the control data from the optical card 5 and then reads out medical information in accordance with the read instruction signal.

Step 64: Any data processes necessary are applied to the medical information read out from the optical card 5. For example, the character, sound and image information may be extracted out from the medical information that has been so far stored in synthesized form as shown in FIG. 4.

Step 65: If the medical information processed in the preceding step 64 is the sound information, the sound information is provided to the sound information processing device 1; if the medical information processed in the preceding step 64 is the character or image information, the character or image information is provided to the image information processing device 2. Thus, the sound information processing device 1 sounds or audibly reproduces the provided sound information. On the other hand, the image information processing device 2 visually shows the provided character or image information on the display device 23. If both of the character and image information are provided to the image information processing device 2, the character information may be shown with the image information in a superimposed manner. Further, if the medical information processed in the preceding step 64 is the sound information and if it is desired to show a corresponding sound waveform diagram on the display 23 with the sound information audibly reproduced, image information on the waveform diagram is provided to the image information processing device 13. In this case, the sound waveform diagram can be stored as image information in the optical card 5; however, in order to save the storage capacity of the card 5, it is more preferable that sound information is temporarily stored in data buffer memory to thereby prepare a sound waveform diagram and then the sound waveform diagram is displayed while sound corresponding to the sound information stored in the buffer memory is audibly reproduced.

According to the embodiment so far described, the optical cards of the write-once-type are employed such that any data, once written, will not disappear, i.e., any previously written information will not be erased by overwriting, as opposed to magnetic recording media typically represented by cassette tapes. In addition, the optical cards are not affected by magnetism, static electricity, radiation etc. and therefore have better data storage capability than other types of recording media. Further, even when the optical cards have been soiled, they can readily be used again by wiping their surfaces.

In addition, as opposed to tape-shape recording media with which a considerable long time is taken to retrieve desired data therefrom, the optical cards allow direct and quick access to desired data in conjunction with the personal computer. For example, names of recorded data may be shown on the display screen of the personal computer so that, in response to the user's selection of a desired data name shown on the screen, the corresponding recorded sound information can be quickly read out for the audible and/or visual reproduction.

The optical cards are generally of a credit card size and therefore can be attached to the patients' charts or the like so as to be easily filed in a desired place. Furthermore, the optical cards are very handy for carrying, and thus if the patient goes to a doctor of another hospital or the like, the patient can have his or her clinical history readily acquired by only presenting the optical card.

Moreover, because data are stored on the optical cards in coded form and thus are difficult to be altered or decoded by any unauthorized person, the optical cards can provide reliable protection of patients' privacy and also can provide superior data safety.

Moreover, because the optical cards can record not only sound information but also image and character information, they provide easy communication and storage of various kinds of information independently.

Although the above embodiment has been described in connection with such a case where cardiac sounds and murmurs detected by a cardiac sound microphone are recorded and reproduced, pulse wave detected by a pulse wave detector, electrocardiogram waveform detected by an electrocardiograph, cardiac echo diagram detected by an ultrasonic cardiac diagnosis device, cardiac tomogram etc. may be recorded as image signals for being graphed as waveform diagram. Moreover, the cardiac sound microphone may be replaced by an electrostethophone utilizing the Doppler effect.

As apparent from the foregoing, the present invention permits recording of medical information corresponding to a patient's morbid state to be efficiently recorded onto an optical card that has a limited storage capacity.

Figure 7A:
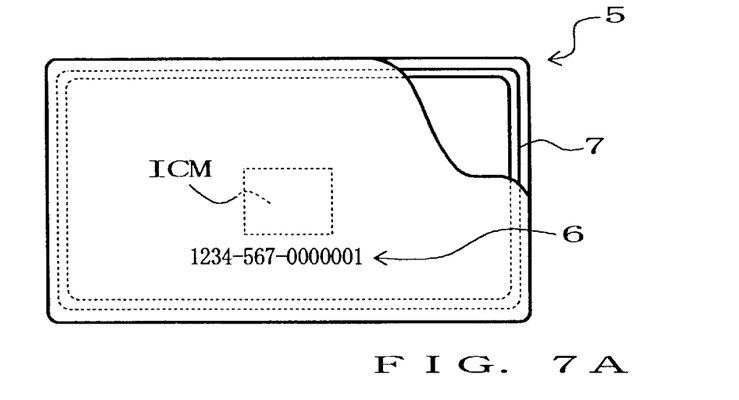
FIGS. 7A and 7B are plan views showing an example of a hybrid-type optical card.
Figure 7B:
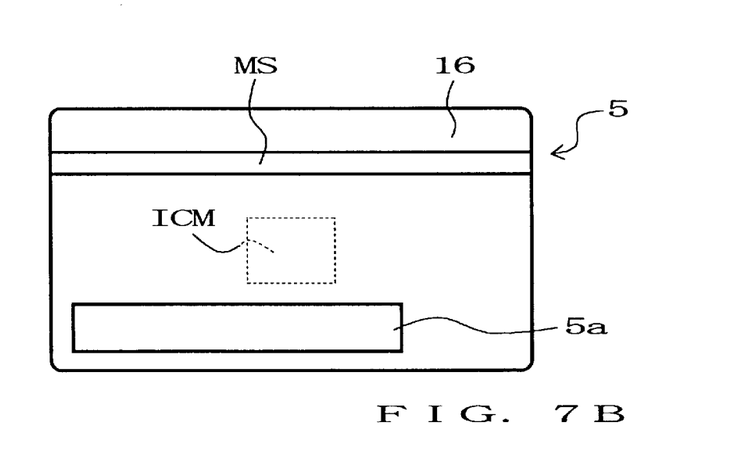

Now, another or second embodiment of the present invention will be described hereinbelow with reference to FIGS. 7A, 7B, 8 and 9. In this embodiment, the optical card 5 is a so-called "hybrid-type optical card" having magnetic and electronic storage functions as well as an optical storage function. That is, on the hybrid-type optical card can be recorded magnetic information and electronic information as well as optical information. FIG. 7A is a plan view showing the obverse side of the optical card 5 with part of its surface layer removed therefrom, and FIG. 7B is a plan view showing the reverse side of the optical card 5.

On the obverse side, as shown in FIG. 7A, the optical card 5 includes an IC (integrated circuit) storage area ICM embedded in a virtually central portion thereof, which comprises an IC chip having a small thickness. The optical card 5 also includes a transmitting/receiving antenna that comprises a coil 7 looped along the entire outer edge thereof. This transmitting/receiving antenna is used to permit an information communication or exchange between the optical card read/write device 4 and the IC storage area ICM in a so-called "non-contacting" fashion.

In addition to the functions of transmitting information stored in the IC storage area ICM and receiving information to be stored in the IC storage area ICM, the transmitting/receiving antenna coil 7 has a function of receiving an externally-generated electromagnetic field so as to generate electric power by detecting or rectifying the received electromagnetic field and supplying the generated electric power to the IC storage area ICM.

As further shown in FIG. 7A, the obverse side of the optical card 5 has an embossed recording area 8 where desired numbers are recorded by stamping.

On the reverse side, as shown in FIG. 7B, the optical card 5 has an optical information recording area 5a of a predetermined size that is scanned by the optical head, as well as a stripe-shaped magnetic information recording area MS that is scanned by a magnetic head (not shown).

The form of use of these information recording areas 5a, ICM and MS on the hybrid-type optical card 5 may be chosen as desired. For example, various medical information may be recorded on the optical information recording area 5a as described earlier in relation to the first embodiment, and other information for assuring more reliable maintenance of secrecy of the patient-related information (patient's secret maintaining information) may be stored in the IC storage area ICM making use of a security function characteristic of the IC. As an example, the patient's secret maintaining information stored in the IC storage area ICM may be compared with information prestored in a patient table possessed by a host computer, so as to control the usability of the optical card 5. Of course, part of the various medical information as described earlier in relation to the first embodiment may also be recorded on the IC storage area ICM. Further, patient's identification code may be recorded on the magnetic recording area MS. Because magnetic cards are employed in relatively many of the existing medical management systems, the additional provision of the magnetic information recording area MS on the optical card 5 permits use of such an existing medical management system when necessary.

Where the hybrid-type optical card 5 is used, the optical card read/write device 4 controls the information reading and writing from and to not only the optical information recording area 5a but also the magnetic information recording area MS; an existing magnetic-stripe read/write device (not shown) can be used to controls the reading and writing from and to the magnetic information recording area MS. Of course, a magnetic-stripe read/write device may be incorporated into the optical card read/write device 4.

Figure 8:
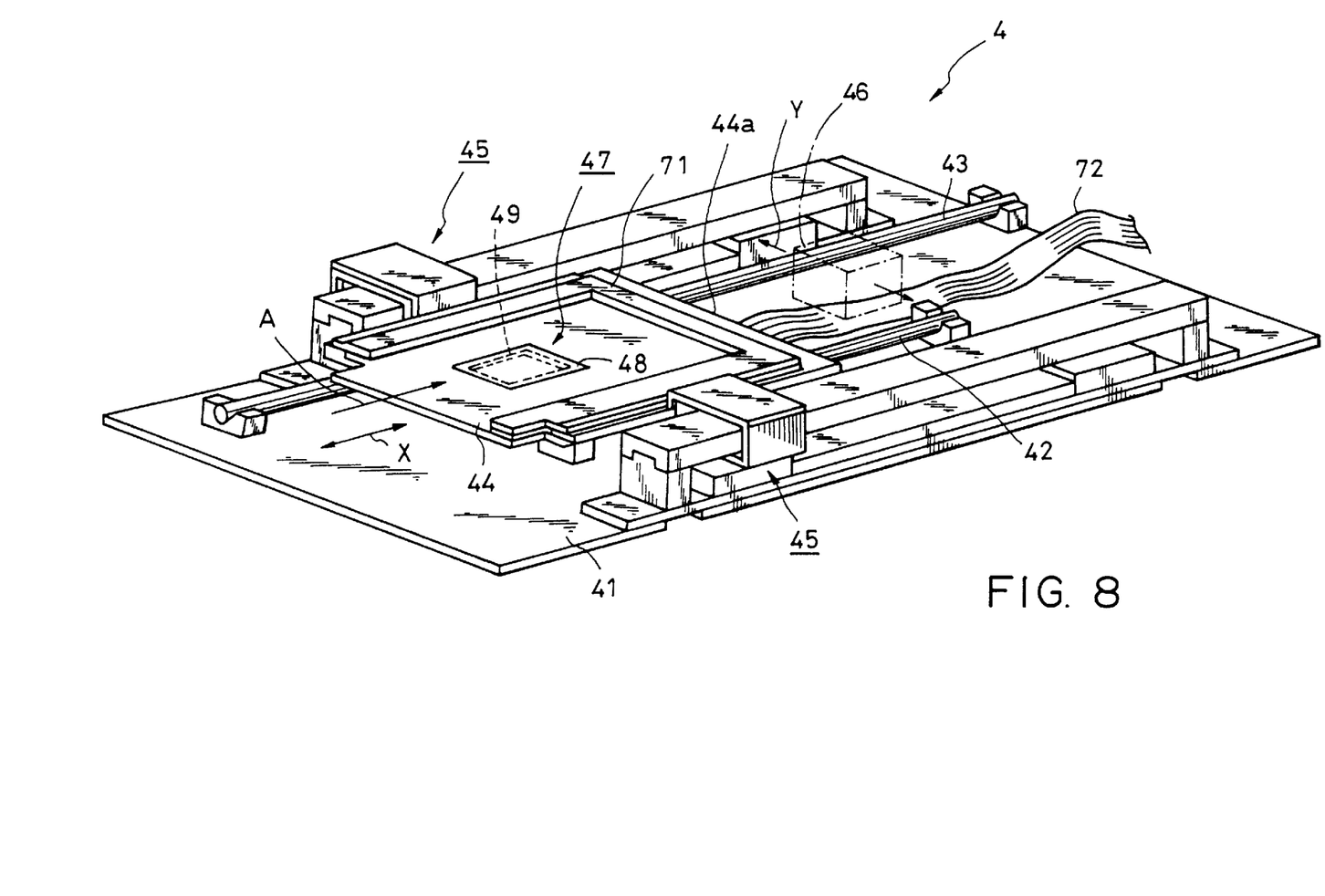
FIG. 8 is a perspective view showing an exemplary structure of a read/write device for the hybrid-type optical card.

FIG. 8 is a perspective view schematically showing an example of the optical card read/write device 4, which has functions to control information reading and writing from and to the optical information recording area 5a and to control non-contacting information reading and writing from and to the IC storage area ICM. Note that in actual use, the read/write device 4 of FIG. 8 is installed upside down from the illustrated orientation.

In FIG. 8, the optical card read/write device 4 includes a pair of parallel elongate guide bars 42 and 43 disposed on a main frame 41 and having different lengths, a card carrier table 44 reciprocatively movable, via a linear motor 45, along the guide bars 42 and 43 in the direction of arrow X, an optical head 46 reciprocatively movable in the direction of arrow Y that is perpendicular to the X direction in which the card carrier table 44 carries an optical card loaded thereon, and an information transmitter/receiver 47 embedded in a virtually central portion of the card carrier table 44.

When an optical card 5 as shown in FIGS. 7A and 7B, the information transmitter/receiver 47 communicates information with the transmitting/receiving antenna coil 7 of the card 5. To this end, the information transmitter/receiver 47 includes a transmitting/receiving antenna comprising a coil 49 embedded in a resin mold 48.

The transmitting/receiving antenna coil 49 has functions of receiving signals transmitted from the transmitting/receiving antenna coil 7 to deliver them to the controller or computer 3 of FIG. 1 and delivering information sent from the controller or computer 3 to the optical card 5, as well as a function of generating a strong electromagnetic field to generate and supply electric power to the IC.

As shown in FIG. 8, a generally U-shaped card guiding/holding plate 71 is provided, on the upper surface of the card carrier table 44 along the outer edge portion thereof, to appropriately position and hold the optical card 5 in place when the card 5 is fed onto the carrier table 44. Further, a flat cable 72 is provided, below the forward half of the card carrier table 44, to electrically connect the transmitting/receiving antenna coil 49 with a controller device (namely, personal computer 3 shown in FIG. 1).

The optical card read/write device 4 of FIG. 8 operates in the following manner. When the card carrier table 44 is moved and positioned at a predetermined card loading position as shown in FIG. 8, the optical card 5 of FIGS. 7A and 7B is fed, by means of a card feeder mechanism including, for example, feed rollers, onto the carrier table 44 in the A direction with its optical information recording area 5a facing upward. Then, the optical card 5 is pushed to a predetermined position on the card carrier table 44 along the card guiding/holding plate 71 and held at the predetermined loading position by the plate 71.

When the optical card 5 has been loaded onto the predetermined loading position of the card carrier table 44, the carrier table 44 is now ready for reciprocative movement along the guide bars 42 and 43 of FIG. 8. During the reciprocative movement of the optical card 5, the optical head 46 reads or write information from or to the optical information recording area 5a (FIG. 7B) of the card 5, and at the same time, information is read or written from or to the IC storage area ICM of the card 5.

Figure 9:
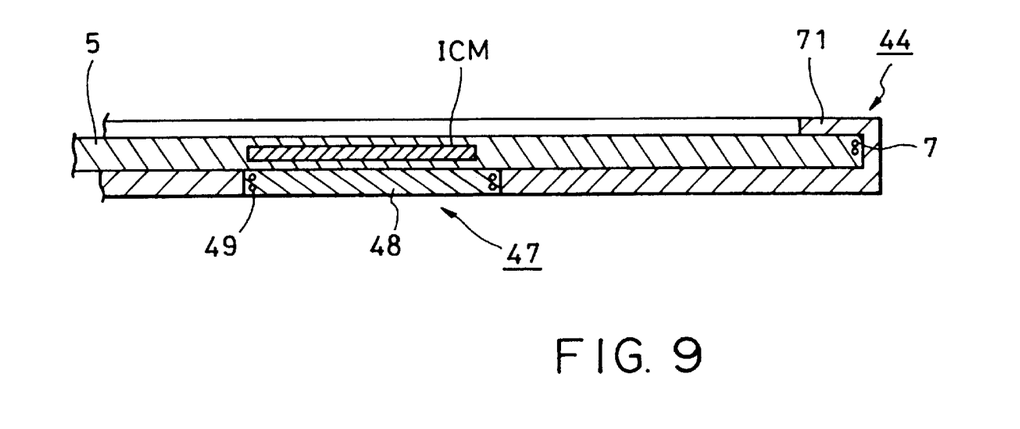
FIG. 9 is a sectional view showing a principal portion of a card carrier table of FIG. 8 on an enlarged scale.

The following paragraphs describe the above-mentioned information reading and writing from and to the IC storage area ICM of the card 5. As shown in FIG. 9, a strong electromagnetic field is produced from the coil 49a of the information transmitter/receiver 47 with the optical card 5 held at the loading position on the card carrier table 44. The antenna coil 7 of the optical card 5 receives the produced electromagnetic field to supply electric power to the IC storage area ICM, so that information stored in the IC storage area ICM is transmitted, as electric signals, via the antenna coil 7. The signals thus transmitted via the antenna coil 7 are received by the coil 49a of the information transmitter/receiver 47 and then delivered via the flat cable 72 to the controller (namely, computer 3 of FIG. 1).

On the other hand, information supplied by the controller is delivered, as electric signals, to the coil 49a of the information transmitter/receiver 47 via the flat cable 72, and these signals are then transmitted to the optical card 5.

Thus, even when information is being read or written, via the optical head 46, from or to the optical information recording area 5a of the optical card 5 loaded on the reciprocating card carrier table 44, the read/write device 4 of FIG. 8 can read or write information from the IC storage area ICM of the card 5 in a non-contacting fashion through communication between the transmitting/receiving antenna coil 7 of the card 5 and the transmitting/receiving antenna coil 49 of the card carrier table 44. This arrangement can substantially reduce the time necessary for the information reading or writing from or to the recording or storage areas of the optical card 5.

After completion of the information reading or writing from or to the recording or storage areas of the optical card 5, the card carrier table 44 is restored to the initial position as shown in FIG. 8, and then the optical card 5 is moved, by means of the card feeder mechanism, out of the carrier table 44 to a predetermined card returning opening (not shown).

As a modification of the second embodiment, the signal communication between the optical card read/write device 4 and the controller (computer 3 of FIG. 1) may be conducted in a non-contacting fashion using a photo coupler (not shown) or using a wireless communication system, rather than via the flat cable 72 described above.

Further, the signal communication between the optical card 5 and the card carrier table 44 may be conducted in a "contacting" fashion using a suitable connector, rather than in the non-contacting fashion.

Furthermore, whereas the embodiment has been described above as supplying electric power to the IC storage area ICM of the optical card 5 from outside the card 5, the card 5 may include a small-thickness electric cell embedded therein as a power source for the IC storage area ICM.

As has been described so far, the second embodiment of the present invention can record various medical information onto an optical card in a variety of recording formats.

What is claimed is:

1. A medical information management system for recording a patient's personal medical information onto a recording medium to manage the medical information, said recording medium being a portable card-like medium independently provided for the patient, said medical information management system comprising:

the recording medium including an optical information recording area, and an integrated circuit memory area for storing electronic information;

a read/write drive for removably attaching thereto said recording medium to read and write information from and to at least said optical information recording area and said integrated circuit memory area, said read/write drive including an optical head for reading and writing optical information from and to the optical information recording area, a carrier mechanism for loading said recording medium on a carrier table and moving the loaded recording medium relative to said optical head, and a coupler section for coupling electronic information to be read and written from and to the integrated circuit memory area of said recording medium, so that reading and writing of the optical information from and to the optical information recording area can be conducted simultaneously with reading and writing of the electronic information from and to the integrated circuit memory area;

a controller for controlling said read/write drive so as to execute control to write any of character information, image information and sound information, corresponding to a morbid state of the patient, into the optical information recording area as the medical information, control to read out said medical information written in the optical information recording area, control to write a predetermined part of said medical information into the integrated circuit memory area and control to read out the predetermined part of said medical information written in the integrated circuit memory area;

a display device for visually displaying the character information and image information contained in said medical information read out by said controller; and a reproduction device for audibly reproducing the sound information contained in said medical information read out by said controller, wherein said coupler section includes a first transmitter/receiver embedded in said carrier table and a second transmitter/receiver embedded in said recording medium for communication with said first transmitter/receiver in such a manner that a relative positional relationship between said first transmitter/receiver and said second transmitter/receiver remains unchanged even when said carrier table is moving for reading and/or writing of said optical information and thereby said coupler section is allowed to communicate a signal indicative of information to be read or written under an always constant communication condition.

2. A medical information management system as defined in claim 1 wherein said recording medium further includes a magnetic information recording area, and which further comprises a device for reading and writing optical information from and to the magnetic information recording area.

3. A medical information management system as defined in claim 1 where said controller inserts at least part of data of said sound information between data of the image information to form composite data, so as to write the composite data into the optical information recording area of said recording medium, and wherein said controller executes control to read out the sound information and image information separately by separating said at least part of data of the sound information and data of the image information from said composite data read out from the optical information recording area of said recording medium.

4. A medical information management system as defined in claim 3 wherein said controller further executes control to insert at least part of data of the character information between the data of the image information to form composite data, so as to write the composite data into the optical information recording area of said recording medium.

5. A medical information management system as defined in claim 4 wherein said controller writes said at least part of the character information into a predetermined part of a storage region of said optical information recording area provided for storing one frame of the image information data.

6. A medical information management system as defined in claim 3 wherein said controller executes control to write said at least part of the sound information into a predetermined part of a storage region of said optical information recording area provided for storing one frame of the image information data.

7. A medical information management system as defined in claim 6 wherein said predetermined part of the storage region substantially corresponds to a peripheral portion of the frame.

8. A medical information management system as defined in claim 1 wherein said display device includes a printer.

9. A medical information management system as defined in claim 1 wherein said display device displays a visual sound waveform diagram corresponding to the sound information reproduced by said reproduction device.

10. A medical information management system as defined in claim 9, which further comprises a device for generating the visual sound waveform diagram on the basis of the sound information read out via said controller.

11. A medical information management system as defined in claim 1 wherein said sound information represents any of cardiac sound and cardiac murmur of the patient.

12. A medical information management system as defined in claim 1 wherein said sound information represents breathing sound of the patient.

* * * * *